US006562796B2

(12) United States Patent
Baldwin et al.

(10) Patent No.: US 6,562,796 B2
(45) Date of Patent: May 13, 2003

(54) DERIVATIVES OF POLYENE MACROLIDES AND PREPARATION AND USE THEREOF

(75) Inventors: Christopher J. Baldwin, Santa Cruz, CA (US); Conway C. Chang, San Francisco, CA (US); Binh T. Dang, San Jose, CA (US)

(73) Assignee: Micrologix Biotech Inc., Vancouver (CA)

( * ) Notice: Subject to any disclaimer, the term of this patent is extended or adjusted under 35 U.S.C. 154(b) by 0 days.

(21) Appl. No.: 10/026,853

(22) Filed: Dec. 20, 2001

(65) Prior Publication Data

US 2002/0094961 A1 Jul. 18, 2002

Related U.S. Application Data

(63) Continuation of application No. 09/483,662, filed on Jan. 14, 2000, now abandoned.

(51) Int. Cl.$^7$ .......................... A61K 31/70; C07H 17/08
(52) U.S. Cl. .......................... 514/31; 536/6.5; 536/18.5
(58) Field of Search ................................ 536/6.5, 18.5; 514/31

(56) References Cited

U.S. PATENT DOCUMENTS

| | | |
|---|---|---|
| 3,244,590 A | 4/1966 | Schaffner et al. |
| 3,780,173 A | 12/1973 | Bruzzese et al. |
| 3,961,047 A | 6/1976 | Bruzzese et al. |
| 4,035,567 A | 7/1977 | Sipos |
| 4,035,568 A | 7/1977 | Schaffner et al. |
| 4,038,382 A | 7/1977 | Bruzzese et al. |
| 4,093,796 A | 6/1978 | Falkowski et al. |
| 4,195,172 A | 3/1980 | Falkowski et al. |
| 4,235,993 A | 11/1980 | Sipos et al. |
| 4,272,525 A | 6/1981 | Wright |
| 4,294,958 A | 10/1981 | Falkowski et al. |
| 4,342,750 A | 8/1982 | Gordon |
| 4,351,937 A | 9/1982 | Stefanska et al. |
| 4,365,058 A | 12/1982 | Falkowski et al. |
| 4,783,527 A | 11/1988 | Falkowski et al. |
| 4,824,944 A | 4/1989 | Stefanska et al. |
| 4,883,785 A | 11/1989 | Chow et al. |
| 5,066,646 A | 11/1991 | Driver et al. |
| 5,100,876 A | 3/1992 | Driver et al. |
| 5,116,960 A | 5/1992 | Driver et al. |
| 5,204,330 A | 4/1993 | Driver et al. |
| 5,296,597 A | 3/1994 | Bruzzese et al. |
| 5,298,495 A | 3/1994 | Bruzzese et al. |
| 5,314,999 A | 5/1994 | Seman et al. |
| 5,567,685 A | 10/1996 | Linden et al. |
| 5,939,399 A | 8/1999 | Vertesy et al. |
| 5,942,495 A | 8/1999 | Borowski et al. |
| 5,965,156 A | 10/1999 | Proffitt et al. |
| 5,981,721 A | 11/1999 | Mohan |

FOREIGN PATENT DOCUMENTS

| | | |
|---|---|---|
| WO | WO 96/35701 | 11/1996 |
| WO | WO 01/91758 | 12/2001 |

OTHER PUBLICATIONS

Beau, "Polyene Macrolides: Stereostructural Elucidation and Synthetic Studies of a Few Members," *Recent Progress in the Chemical Synthesis of Antibiotics* (1990) 135–182.

Bennett, "Antifungal Agents," *Goodman and Gilman's: The Pharmacological Basis of Therapeutics,* (1990) 8$^{th}$ Edition Ch 50:1165–1181.

Brajtburg et al., "Amphotericin B: Current Understanding of Mechanisms of Action," *Antimicrobial Agents and Chemotherapy* (Feb. 1990) 183–188.

Bruzzese et al., "Amide derivatives of partricin A with potent antifungal activity," *Cur J Med Chem* (1996) 31:965–972.

Charretier et al., "Intracellular alkalinization induced by amphotericin B derivatives in HL–60 leukemia cells," *Biochemie* (1989) 71:67–70.

Cheron et al., "Quantitative Structure–Activity Relationships in Amphotericin B Derivatives," *Biochemical Pharmacology* vol. 37 No. 5: 827–836.

Czerwinski, et al., "Amphotericin B 2–Morpholinoethylamide Diaspartate, A New Water Soluble Derivative of the Antibiotic Synthesis and Biological Properties," *J Antibiotics* (Jun. 1990) 680–683.

Ellis et al., "Neurotoxicity of Amphotericin B Methyl Ester in Dogs," *Toxicologic Pathology* (1988) vol. 16 No. 1:1–9.

Falkowski et al., "N–Glycosyl Derivatives of Polyene Macrolide Antibiotics," *J Antibiotics* 28:244–245.

Fingl et al., "General Principles," *The Pharmaceutical Basis of Therapeutics* (1975) CH 1:1–46.

Gary–Bobo, "Polyene–sterol interaction and selective toxicity," *Biochemie* (1989) 71:37–47.

Gil et al., "Polyene Antibiotics," Ch. 19: 551–575.

Graybill, "The Future of Antifungal Therapy," *Clinical Infectious Diseases* (1996) 22 (Suppl 2) :S166–S178.

Harstel et al., "Amphotericin B: new life for an old drug," *Trends Pharmacol Sci* (Dec. 1996) 17(12):445–449.

Hodge, J.E., et al., "Amadori Rearrangement Products," *Methods in Carbohydrate Chemistry* Editors: Whistler and Wolfrom (1963) vol. 2:99–107.

Hoeprich, et al., "Toxicity of Amphotericins on Chronic Administration to Mongrel Dogs," *Diagn. Microbiol. Infect. Dis.* (1985) 3:47–58.

Jarzebski et al., "Synthesis and Structure–Activity Relationships of Amides of Amphotericin B," *J Antibiotics* (Feb. 1982) 220–229.

(List continued on next page.)

*Primary Examiner*—Elli Peselev
(74) *Attorney, Agent, or Firm*—Seed Intellectual Property Law Group PLLC

(57) ABSTRACT

The present invention provides a new class of polyene macrolide derivatives useful for treating or preventing fungal infections. The new polyene macrolide derivatives exhibit surprisingly superior antifungal activity and water solubility compared to amphotericin B methyl ester (AME). In addition, the new polyene macrolide derivatives have improved water solubility and lower toxicity than both amphotericin B (AmB) and AME.

30 Claims, 1 Drawing Sheet

OTHER PUBLICATIONS

Keim, Jr. et al., "Amphotericin B Methyl EsterHyrochloride and Amphotericin B: Comparative Acute Toxicity," *Science* (1973) 179:584–585.

Keim, Jr., et al., "Comparative Toxicological Studies of Amphotericin B Methyl Ester and Amphotericin B in Mice, Rats and Dogs," *Antimicrobial Agents and Chemotherapy* (Oct. 1976) vol. 10 No. 4: 687–690.

Macpherson et al., "Adventures in Polyene Macrolide Chemistry: The Derivatisation of Amphotericin B" (1993) *Recent Advances in the Chemistry of Anti–Infective Agents* Edited by PH Bently and R Ponsford, Royal Society of Chemistry, Ch 14, 205–222.

Massa et al., "Subchronic Toxicity Studies of N–D–Ornithyl Amphotericin B Methyl Ester in Dogs and Rats," *Fundamental and Applied Toxicology* 5, 737–753.

Parmegiani et al., "Comparative In Vitro and Vitro Evaluation of N–D–Ornithyl Amphotericin B Methyl Ester, Amphotericin B Methyl Ester, and Amphotericin B," *Antimicrobial Agents and Chemotherapy* (Nov. 1987) vol. 31, No. 11:1756–1760.

Szponarski et al., "Interaction of $^{14}$C–labelled Amphotericin B Derivatives With Human Erythrocytes: Relationship Between Binding and Induced $K^+$ leak," *Biochimica et Biophysica Acta* (1988) 938:97–106.

Cybulska et al., 2000, "N–Methyl–N–D–Fructosyl Amphotericin B Methyl Ester (MF–AME), a Novel Antifungal Agent of Low Toxicity: Monomer/Micelle Control Over Selective Toxicity," *Acta Biochimica Polonica* 47(1):121–131.

Szlinder–Richert et al., 2000, "Comparative Studies on Cell Stimulatory, Permeabilizing and Toxic Effects Induced in Sensitive and Multidrug Resistant Fungal Strains by Amphotericin B (AMB) and N–methyl–N–D–Fructosyl Amphotericin B Methyl Ester (MFAME)," *Acta Biochimica Polonica* 47(1):133–140.

Grzybowska et al., 1997, "N–Methyl–D–Fructopyranosylamphotericin B Methyl Ester, New Amphotericin Derivative of Low Toxicity," *J. Antibiotics* 50(8):709–711.

DERIVATIVES OF POLYENE MACROLIDES AND PREPARATION AND USE THEREOF

This application is a continuation application of Application Ser. No. 09/483,662, filed Jan. 14, 2000, now abandoned, the entire content of which is hereby incorporated by reference.

BACKGROUND OF THE INVENTION

1. Field of the Invention

The present invention relates generally to derivatives of polyene macrolides. In particular, the present invention relates to water soluble glycosyl derivatives of polyene macrolides useful for treating or preventing topical and/or systemic fungal infections in humans and animals.

2. Description of Related Art

Many polyene macrolides are known that have antifungal properties useful in treating topical and/or systemic fungal infections. Examples of these polyene macrolides include amphotericin B, aureofacin, candicidin, candidin, levorin, mycoheptin, nystatin, perimycin, pimaricin, polyfungin, rimocidin and trichomycin. However, due to their macrocyclic nature and amphoteric character, these compounds generally have poor solubility in aqueous solutions, which limits their usefulness in the treatment of systemic fungal infections. In addition, these polyene macrolides exhibit undesirable toxic properties when used systemically. For example, while amphotericin B methyl ester (AME) exhibited lower acute, nephro and hepto toxicity than amphotericin B in rats and dogs, in the only clinical trial conducted with AME in patents with systemic fungal infections, many patients developed progressive neurological dysfunction associated with white matter degeneration, see Ellis et al., 1988, Tox. Path. 16(1):1; Parmegiani et al., 1987, Antimicrob. Agents Chemo. 31(11):1756–1760; Hoeprich et al., 1985, Diag. Microbiol. Infect. Dis. 3:47–58; Massa et al., 1985, Fund. App. Tox. 5:737–753; Keim Jr., et al., 1976, Antimicrob. Agents Chemo. 10(4):687–690; and Keim Jr., et al., 1973, Science 179:584–586. The incidence and severity of these complications increased with the amount of AME administered (Id.). In fact, the toxicity of AME was so severe that the clinical trial was canceled and product was never brought to market.

Many derivatives of polyene macrolides have been developed, in part to address these limitations. For example, U.S. Pat. No. 4,093,796 to Falkowski et al. teaches polyene macrolides substituted at the sugar amino group with a saccharide. U.S. Pat. No. 4,195,172 to Falkowski et al. teaches N-methylglucamine salts of N-glycosyl derivatives of polyene macrolides in which the amino group of the polyene macrolide is substituted with an aldose or ketose mono- or oligosaccharide. U.S. Pat. No. 4,294,958 to Falkowski et al. teaches trimethylammonium salts of polyene macrolides, including the methyl esters. U.S. Pat. No. 4,365,058 to Falkowski et al. teaches esters of polyene macrolides that are substituted at the sugar amino group with non-sugar substituents. U.S. Pat. No. 4,783,527 to Falkowski et al. teaches amides of polyene macrolides substituted at the amide nitrogen with an alkyl, isoalkyl or heterocyclic group. U.S. Pat. No. 5,314,999 to Seman et al. teaches polyene macrolides substituted at the N position with a 1-amino-1-deoxyketose group, which itself may be further substituted. U.S. Pat. No. 5,942,495 to Borowski et al. teaches N-alkyl-N-glycosyl derivatives of polyene macrolides that are reported to have antifungal activity, form water soluble salts with acids and lower toxicity than other N-alkyl polyene macrolide derivatives.

None of the foregoing derivatives provide an optimum combination of water solubility, low toxicity, and potency as an antifungal agent. Since AmB is still the drug of choice for many indications, there is a need for polyene macrolides that exhibit antifungal activity and that have improved water solubility and/or toxicity properties.

SUMMARY OF THE INVENTION

In one aspect, the present invention provides a new class of polyene macrolide derivatives that exhibit surprisingly superior antifungal activity, increased water solubility and lower toxicity than amphotericin B (AmB) and amphotericin B methyl ester (AME). The polyene macrolide derivatives of the invention comprise a "core" polyene macrolide backbone derived from any of a variety of polyene macrolides having two features: a carboxyl substituent and an amino sugar substituent. In the polyene macrolide derivatives of the invention, the carboxyl substituent of the "core" is converted to an alkyl or arylalkyl ester, thioester or amide, and the amino group of the amino sugar is substituted with a carbohydrate residue, which may be a mono, oligo or polysaccharide.

Specifically, the present invention provides polyene macrolide derivatives according to structural formula (I):

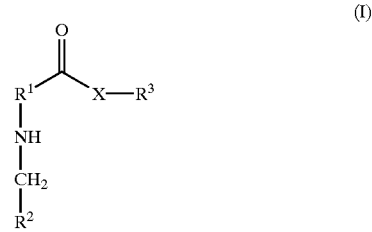

including the pharmaceutically acceptable salts thereof, wherein:
- $R^1$ is a polyene macrolide backbone;
- $CH_2$—$R^2$ is a carbohydrate residue, where the illustrated $CH_2$ includes the anomeric carbon of a terminal carbohydrate saccharide;
- $R^3$ is alkyl or arylalkyl; and
- X is O, S or NH.

In one important embodiment, the polyene macrolide derivatives are compounds according to structural formula (I), with the proviso that when $R^1$ is a polyene macrolide backbone derived from amphotericin B, X is O, and $R^3$ is methyl, lower alkanyl or lower alkyl, then $R^2$ is other than fructosyl.

In another aspect, the present invention provides methods for making these new polyene macrolide derivatives. According to the method, a parent polyene macrolide is reacted according to known methods to yield the corresponding alkyl or arylalkyl ester, thioester or amide. The ester, thioester or amide is then reacted with an appropriate reducing sugar under Amadori rearrangement conditions to yield a new polyene macrolide derivative according to the invention.

In another aspect, the present invention provides pharmaceutical compositions including the new polyene macrolide derivatives, or pharmaceutically acceptable salts thereof, as well as methods for treating and/or preventing fungal infections in plants or animals, including humans. The pharmaceutical compositions generally comprise one or more polyene macrolide derivatives of the invention and a pharmaceutically acceptable carrier, excipient or diluent. The choice of carrier, excipient or diluent will depend upon the mode of administration.

The method generally involves administering to a plant or animal, including a human, one or more of the polyene macrolide derivatives or pharmaceutical compositions of the invention in an amount effective to treat or prevent a fungal infection in the plant, animal or human. The polyene macrolide derivatives or pharmaceutical compositions may be administered systemically or applied topically, depending on the nature of the fungal infection.

DETAILED DESCRIPTION OF THE INVENTION

Figure 1:
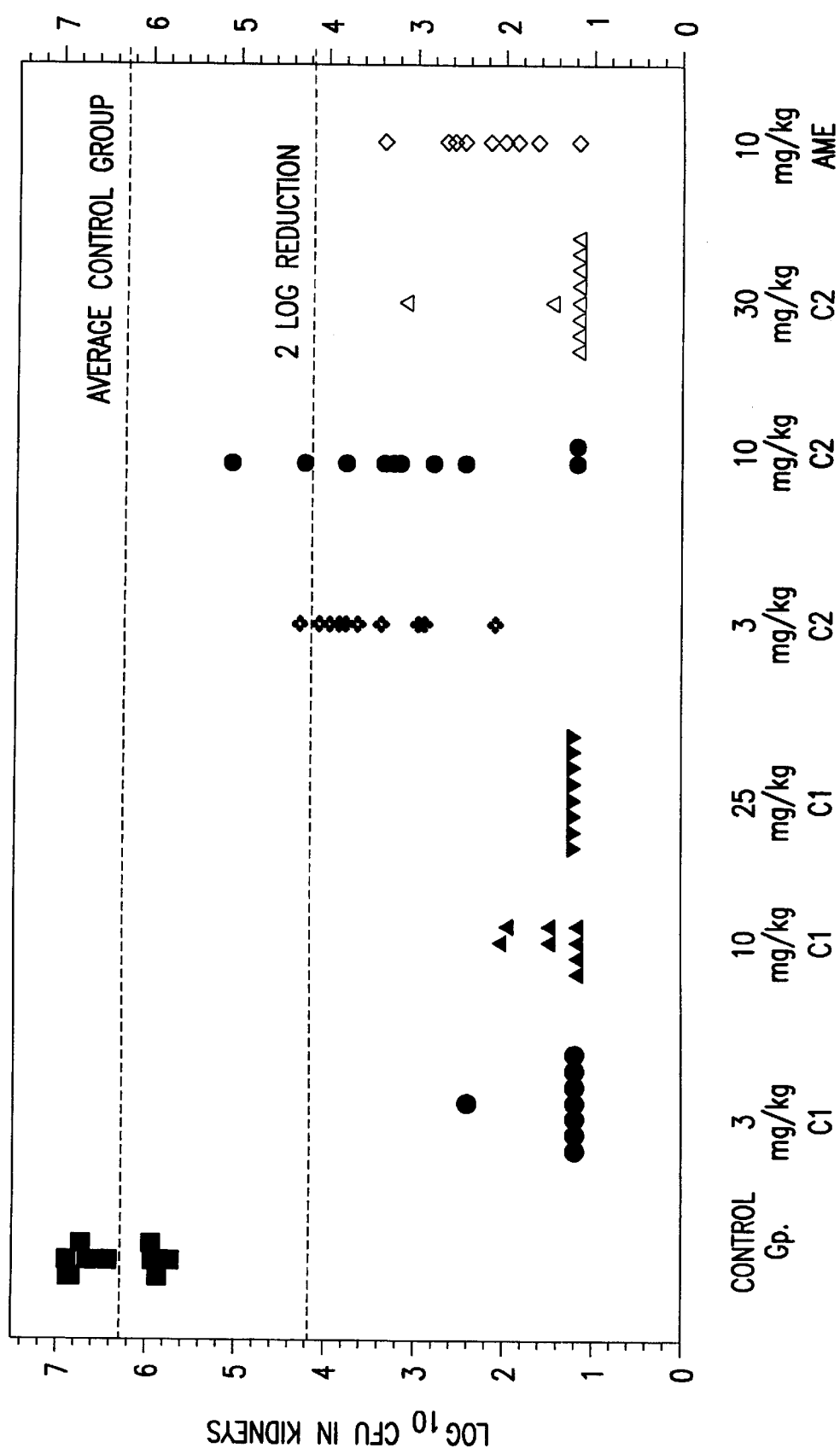
FIG. 1 shows the levels of *Candida albicans* in the kidneys of mice treated with various polyene macrolide derivatives of the present invention.

The present invention provides new gylcosyl derivatives of polyene macrolides (and/or pharmaceutically acceptable salts thereof), pharmaceutical compositions comprising these polyene macrolide derivatives, methods of making these polyene macrolide derivatives, and methods of using the new polyene macrolide derivatives and/or pharmaceutical compositions to treat and/or prevent fungal infections in both plants and animals, including humans.

The polyene macrolide derivatives described herein provide significant advantages over traditional polyene macrolide antifungals. For example, the polyene macrolide derivatives of the present invention provide greater water solubility, lower toxicity, and greater potency than traditional polyene macrolide antifungals such as amphotericin B (AmB) and amphotericin B methyl ester (AME).

Specifically, the compounds of the present invention are polyene macrolide derivatives according to structural formula (I):

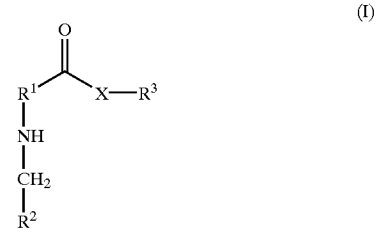

including the pharmaceutically acceptable salts thereof, wherein:

$R^1$ is a polyene macrolide backbone;

$CH_2$—$R^2$ is a carbohydrate residue, where the illustrated $CH_2$ includes the anomeric carbon of a terminal carbohydrate saccharide;

$R^3$ is alkyl or arylalkyl; and

X is O, S or NH.

Those of skill in the art will appreciate that the polyene macrolides of the invention are derivatives of "core" polyene macrolides of a specific type. Specifically, the core polyene macrolides are of a type that have a carboxyl substituent and an amino sugar substituent, as exemplified by, for example, AmB and nystatin. In the derivatives of the invention, the carboxyl substituent of the core polyene macrolide is converted to an alkyl or arylalkyl ester, thioester, or amide, and the amino group of the amino sugar substituent is substituted with a carbohydrate residue. The carbohydrate residue, which is described in more detail below, is attached to the amino group via the anomeric carbon of a terminal saccharide unit.

In the polyene macrolide derivatives of formula (I), polyene backbone $R^1$ may be derived from any known or later discovered polyene macrolide having carboxyl and amino sugar substituent. Preferably, the polyene macrolide from which $R^1$ is derived will have antifungal activity. Non-limiting examples of polyene macrolides having these features from which polyene backbone $R^1$ may be derived include, but are not limited to, amphotericin A (AmA), amphotericin B (AmB), aureofacin, candicidin, candidin, levorin, mycoheptin, nystatin (including $A_1$), partricin (A and B), pentamycin, perimycin, pimaricin, polyfungin, rimocidin, and trichomycin. Preferred classes of polyene backbones $R_1$ are those derived from AmB and nystatin. The structures of nystatin and AmB are as illustrated below, including citations referencing methods whereby these polyene macrolides may be obtained:

AmB

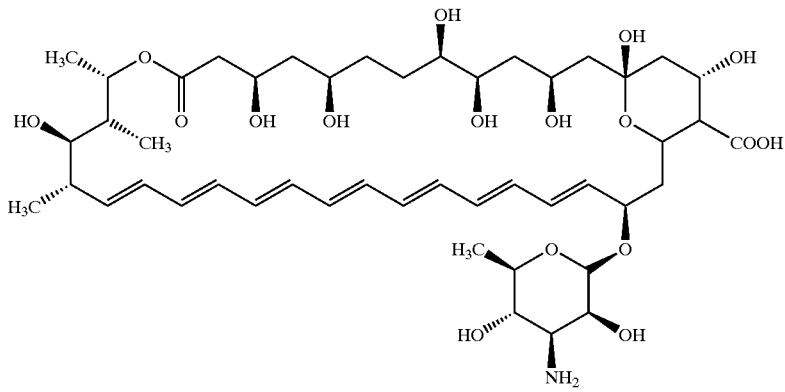

Merck Index #620; U.S. Pat. No. 2,508,611;

Nystatin A$_1$

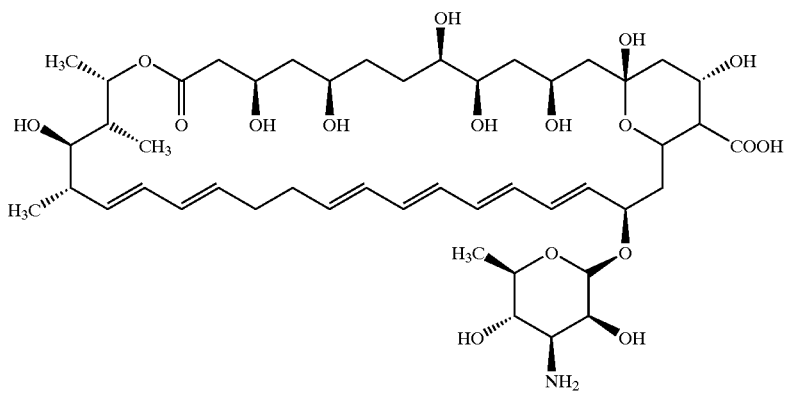

Merck Index #6658; U.S. Pat. Nos. 2,832,719; 3,517,100

Those of skill in the art will recognize that the NH—R$^1$—COXR$^3$ portion of the polyene macrolide derivatives of formula (I) is contributed by the core polyene macrolide, with the exception of XR$^3$, which is part of the novel derivatives described herein. Thus, it will further be appreciated that macrolide backbone R$^1$ includes the sugar moiety that is attached to the macrocyclic portion of core polyene macrolide. This sugar, which is an inherent part of the core polyene macrolide, is to be distinguished from the carbohydrate residue CH$_2$—R$^2$ of formula (I), which is not contributed by the core polyene macrolide and constitutes one of the inventive features of the derivatives of formula (I). Thus, as a specific example, the polyene backbone R$^1$ derived from AmB is illustrated below, wherein the dashed lines indicate the atoms which are bonded to the XR$^3$ and CH$_2$—R$^2$ substituents in the derivatives of formula (I), and the bolded NH group is the NH illustrated in formula (I):

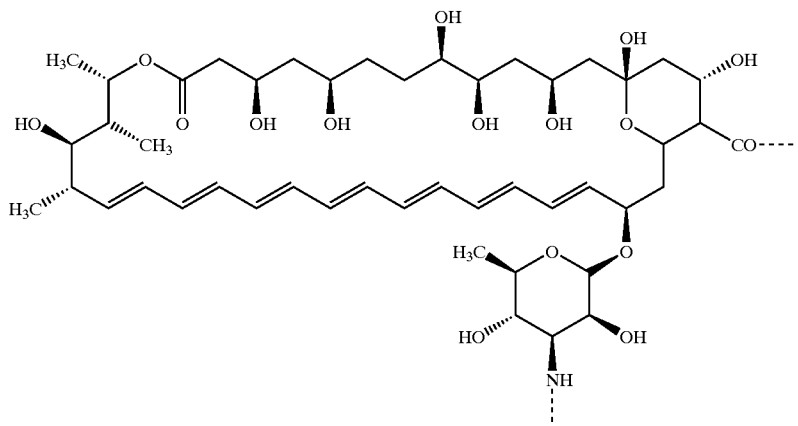

The structures of polyene backbones $R^1$ derived from other core polyene macrolides will be apparent to those of skill in the art.

The carbohydrate residue $CH_2$—$R^2$ may be any number of saccharide units in length and, typically ranges from 1 to about 100 saccharide units. Thus, the carbohydrate residue can be a monosaccharide, an oligo saccharide comprising from two to tens of saccharide units or a poly saccharide comprising from tens to 30, 40, 50, 60 or even more saccharide units. Preferably, the carbohydrate residue will be of a number of saccharide units such that it is relatively water soluble, such as a mono saccharide or an oligo saccharide. However, as it has been discovered that substituting the amino sugar of AmB with large polymers does not deleteriously affect the antifungal activity of the macrolide, carbohydrate residue $CH_2$—$R^2$ may be a large, water insoluble polysaccharide and still retain antifungal activity. Polyene macrolide derivatives including large polysaccharides for carbohydrate residue $CH_2$—$R^2$ that have low water-solubility may be used topically or as antifungals in non-aqueous environments.

The carbohydrate residue may be a homopolymer, in which all saccharide units are the same, or it may be a heteropolymer comprising mixtures of different saccharide units. The carbohydrate residue may be branched or linear, and, as will be discussed in more detail below, the saccharide units may be independently of one another, in a cyclic conformation, a linear conformation or a mixture of cyclic and linear conformations. Moreover, subject only to the constraints of the Amadori rearrangement reaction used to synthesize the polyene macrolide derivatives of the invention, the saccharide units of the carbohydrate residue may be substituted with a variety of different substituents. These substituents may be used to impart the derivatives of the invention with desirable properties, such as, for example, improved water-solubility.

As will be discussed in more detail in connection with the methods of synthesizing the new derivatives, it will be appreciated that the carbohydrate residue $CH_2$—$R^2$ is produced via an Amadori rearrangement of an appropriate reducing carbohydrate, typically a reducing sugar. Therefore, the carbohydrate residue $CH_2$—$R^2$ has a different structure from the reducing carbohydrate used as a reactant in the Amadori rearrangement used to produce the polyene macrolide derivatives of formula (I). The principles of the Amadori rearrangement reaction and the requirements of reducing carbohydrates that can undergo an Amadori rearrangement are well-known and well understood. Briefly, the rearrangement and the requirements of the reducing carbohydrates, exemplified with a monosaccharide, are illustrated below:

Amadori Rearrangement

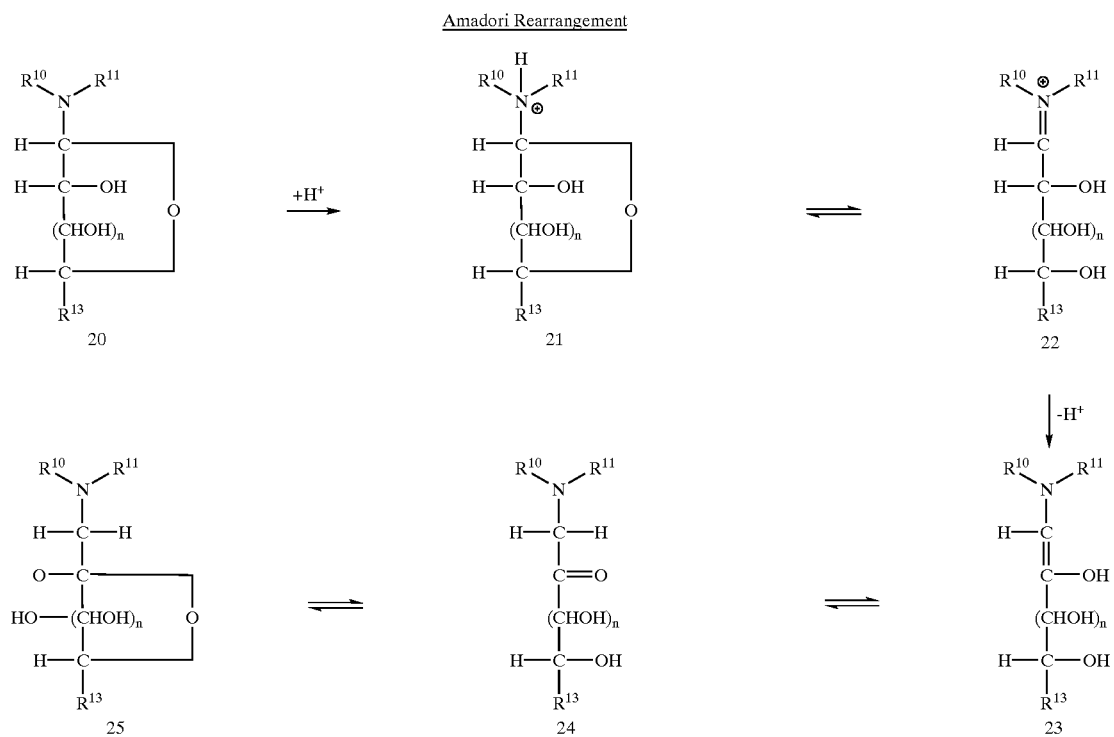

The requirements of the reducing carbohydrates which can undergo the rearrangement are defined by the various R groups. In compounds 20, 21, 22, 23, 24 and 25, n is an integer from 0 up to virtually any number, where n is 0 only in open chain conformers; $R^{10}$ is hydrogen, alkyl, alkylidene, cycloalkyl, arylalkyl, aryl, glycosyl or polymer, but not acyl or a strongly electron-withdrawing radical; $R^{11}$ is hydrogen, alkyl, alkylidene, arylalkyl, but not aryl when $R^{10}$ is aryl and, in addition, the combination of $R^{10}+R^{11}$ in the reacting amine should not sterically hinder the nitrogen atom; and $R^{13}$ is hydrogen, —$CH_2OH$, —$CH_3$, —COOH, —CONHR, —COO$^-$M$^+$, and the like. Any reducing carbohydrate having these attributes can be used in an Amadori rearrangement to yield the polyene macrolide derivatives of the invention. For additional guidance regarding the requirements of the Amadori rearrangement, see Hodge & Fisher, "Amadori Rearrangement Products," *In: Methods in Carbohydrate Chemistry, Volume II, Reactions of Carbohydrates,* Whistler & Wolfram, Eds., pp. 99–107, Academic Press, Inc., New York (1963). Skilled artisans will be able to select an appropriate reducing carbohydrate reactant to obtain a derivative according to formula (I) that has the desired carbohydrate residue $CH_2$—$R^2$. TABLE 1 presents an exemplary list of reducing carbohydrates that are capable of undergoing an Amadori rearrangement that may be used to produce the compounds of the present invention. Other carbohydrates having appropriate properties will be apparent to those of skill in the art.

TABLE 1

Exemplary Reducing Carbohydrate for Amadori Reaction

3-O-methyl-glucose
4,6-di-O-methyl-D(L)-mannose
4,6-O-benzylidene-D(L)-galactose
4,6-O-benzylidene-D(L)glurpranoside
4,6-O-ethylidene-alpha-D(L)-glucose
4-azidomethyl-tetrahydro-pyran-2,3,5-triol
4-benzyloxy-6-benzyloxymethyl-tetrahydro-pyran-2,3,5-triol
4-fluoro-4-deoxy-D(L)-glucose
6-acetamido-6-deoxy-alpha-D(L)-glucopyranose
6-aminomethyl-4H-pyran-2,3,4,5-tetraol
6-chloro-6-deoxy-alpha-D(L)-glucopyranose
alginic acid
allose
alpha-L(D)-rhamnose
altrose
arabinose
D(L)-arabinose
D(L)-fucose
D(L)-glucuronic acid
D(L)-leucrose
D(L)-mannose-6-phosphate
D(L)-xylose
D-thevetose
fucose
gentiobiose
glucose
gulose
idose
lyxose
maltopentose
mannose
mannose-6-phosphate
melibiose
melibiose
N-(2,3,5-trihydroxy-6-hydroxymethyl-tetrahydro-pyran-4-yl)-acetamide
panose
pectic acid
rhamnose
ribose
salicin
sorbose
sulfanilamide-N4-D(L)-glucoside
talose
xylose Those of skill in the art will appreciate that the illustrated Amadori rearrangement illustrates only the carbohydrate.

For the reactions and polyene macrolide derivatives described herein, in Compounds 20, 21, 22, 23, 24 and 25, $R^{10}$ represents the polyene backbone $R^1$.

As illustrated in the above rearrangement, it will be appreciated that the resultant carbohydrate residue produced by an Amadori rearrangement reaction may be in either a cyclic or linear conformation, or a mixture of cyclic and linear conformers. While in the preferred polyene macrolide derivatives illustrated herein the various carbohydrate residues added via the Amadori rearrangement are shown in their cyclic conformations, these illustrations are not intended in any way to limit the carbohydrate residue of the illustrated polyene macrolide derivatives, or of any polyene macrolide derivatives, described herein, to the cyclic forms. When the carbohydrate residue is a monosaccharide, it may be linear, cyclic or a mixture of linear and cyclic conformers. When the carbohydrate residue is an oligo or polysaccharide, each monosaccharide unit my be cyclic or linear, or a mixture of cyclic and linear conformers. Thus, the polyene macrolide derivatives described herein may be in the form of pure compounds or in the form of mixtures of two or more different conformers. The only requirement is that the polyene macrolide derivative, whether a single compound or mixture of different conformers, have antifungal activity as described herein.

In the polyene macrolide derivatives of formula (I), preferred monosaccharide carbohydrate residues $CH_2$—$R^2$ include glucopyranose, mannopyranose, galactopyranose, fructopyranose, and tagatopyranose. Preferred polysaccharide carbohydrate residues $CH_2$—$R^2$ include 4-O-(β-D-glucopyranosyl)-D-fructopyranose, 4-O-(β-D-galactopyranosyl)-D-fructopyranose, 4-O-(β-D-glucopyranosyl)-D-fructopyranose, 4-O-(α-D-glucopyranosyl)-D-fructopyranose, sucrose, maltose, lactose, cellobiose, L-rhinnose and D-ribose. As noted above, these carbohydrate residues are attached to the polyene backbone amino sugar amino group via the anomeric carbon of a terminal monosaccharide unit.

In the polyene macrolide derivatives of formula (I), $R^3$ may be an alkyl group or an arylalkyl group. As used herein, "alkyl" refers to a saturated or unsaturated, branched, straight-chain or cyclic monovalent hydrocarbon group derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl (allyl), cycloprop-1-en-1-yl; cycloprop-2-en-1-yl, prop-1-yn-1-yl , prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl , but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like.

The term "alkyl" is specifically intended to include groups having any degree or level of saturation, i.e., groups having exclusively single carbon—carbon bonds, groups having one or more double carbon—carbon bonds, groups having one or more triple carbon—carbon bonds and groups having mixtures of single, double and triple carbon—carbon bonds. Where a specific level of saturation is intended, the expressions "alkanyl," "alkenyl," and "alkynyl" are used.

"Alkanyl" refers to a saturated branched, straight-chain or cyclic alkyl group derived by the removal of one hydrogen atom from a single carbon atom of a parent alkane. Typical alkanyl groups include, but are not limited to, methanyl; ethanyl; propanyls such as propan-1-yl, propan-2-yl (isopropyl), cyclopropan-1-yl, etc.; butyanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkenyl" refers to an unsaturated branched, straight-chain or cyclic alkyl group having at least one carbon—carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1en-1-yl, prop-1-en-2-yl, prop-2-en-1-yl (allyl), prop-2-en-2-yl, cycloprop-1-en-1-yl; cycloprop-2-en-1-yl; butenyls such as but-1en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1en-3-yl, cyclobuta-1,3-dien-1-yl, etc.; and the like.

"Alkynyl" refers to an unsaturated branched, straight-chain or cyclic alkyl group having at least one carbon—carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1yn-1-yl, but-1-yn-3-yl, but-3-yn-1-yl, etc.; and the like.

The alkyl group may comprise from 1 to 12 carbon atoms. Typically, the alkyl group is a lower alkyl having from 1 to 6 carbon atoms. In particularly preferred embodiments, the alkyl is ($C_1$—$C_3$) alkanyl or alkenyl. The most preferred alkyl groups are methyl and allyl, such that the compounds of formula (I) are methyl or allyl esters, methyl or allyl thioesters, or methyl or allyl amides.

Alternatively, $R^3$ may be an arylalkyl group. As used herein, "arylalkyl" refers to an alkyl group in which one of the alkyl hydrogens is replaced with an aryl substituent. Where specific levels of saturation of the alkyl portion of the arylalkyl group are intended, the nomenclature "arylalkanyl," "arylalkenyl" and "arylalkynyl" is used, where "alkanyl," alkenyl" and "alkynyl" are as previously defined. Typical aryl substituents in the arylalkyl group include, but are not limited to, penta-2,4-dienyl, phenyl, naphthyl, and the like. The arylalkyl may comprise from 6 to 26 carbon atoms. Typically, the aryl portion of the arylalkyl group is phenyl or naphthyl and the alkyl portion is a lower alkyl. More preferably, the alkyl portion of the arylalkyl group is a lower alkanyl. The most preferred arylalkyl group is benzyl, such that the compounds of formula (I) are benzyl esters, benzyl thioesters or benzyl amides.

Substituent X may be either O, S, or NH. Preferably, X is O or NH, with O being particularly preferred.

One important class of polyene macrolide derivatives according to the invention are compounds according to structural formula (I), with the proviso that when $R^1$ is a polyene macrolide backbone derived from amphotericin B, X is O and $R^3$ is methyl, lower alkanyl or lower alkyl, then $R^2$ is other than fructosyl.

In another important embodiment, the polyene macrolide derivatives of the invention are compounds according to formula (I), with the proviso that the compound is not the compound identified as N-fructosyl methyl ester AmB in Szponarski et al., 1988, Biochimica Biophysica Acta 938:97–106, at page 99 in FIG. 1, which for convenience is illustrated below:

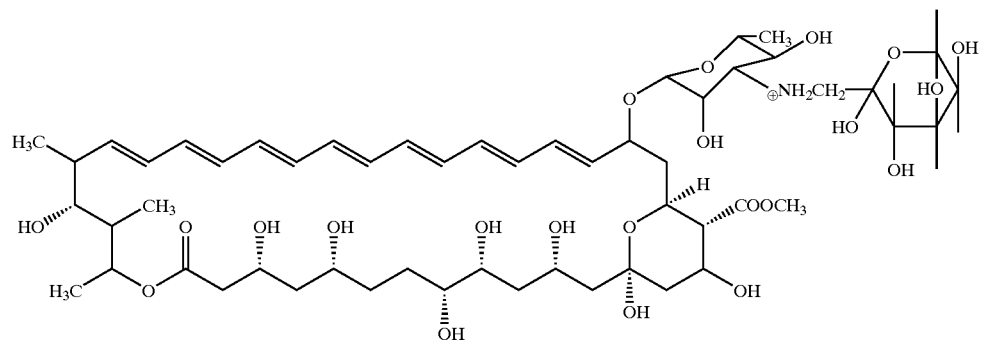

Another important class of polyene macrolide derivatives according to the invention include glycosyl AmB methyl ester derivatives. In particular, the following specific compounds are preferred:
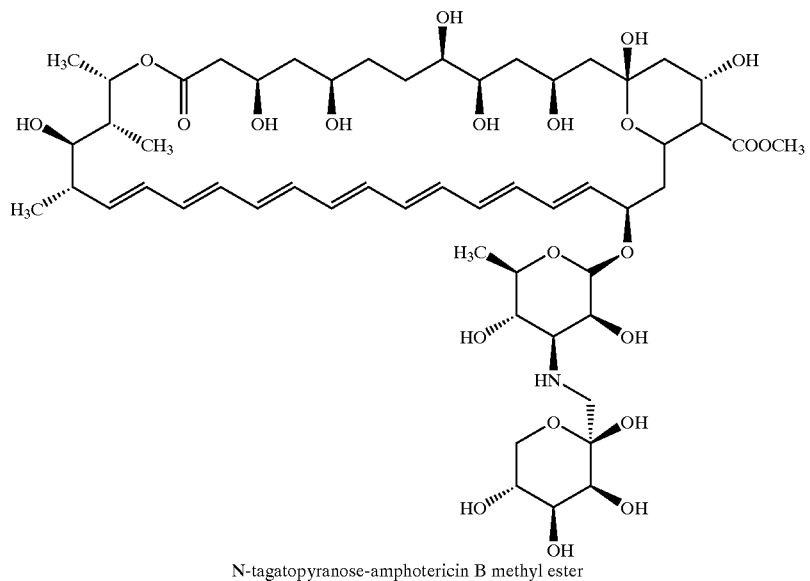
N-tagatopyranose-amphotericin B methyl ester (C1)
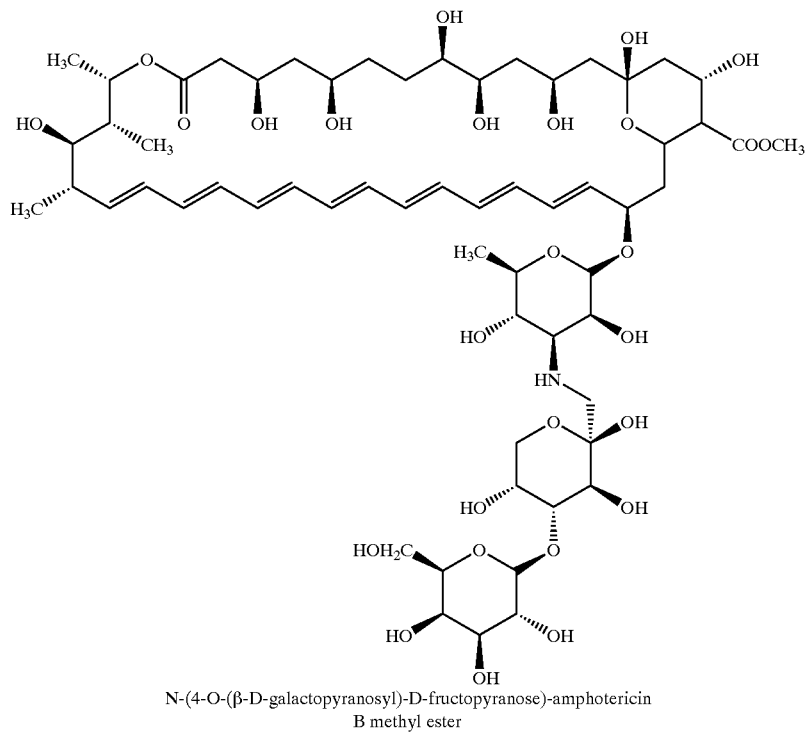
N-(4-O-(β-D-galactopyranosyl)-D-fructopyranose)-amphotericin B methyl ester (C2)

-continued

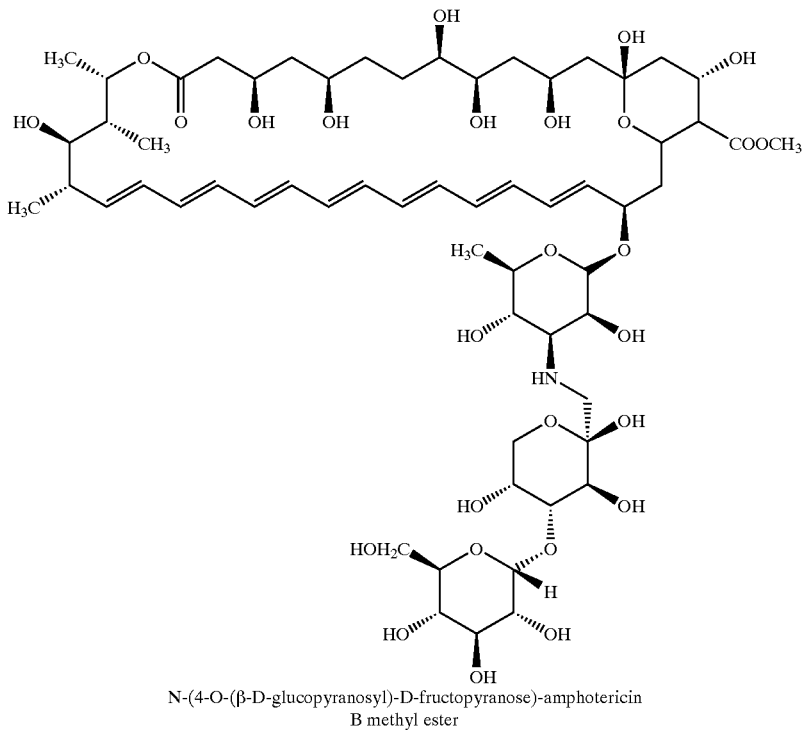

N-(4-O-(β-D-glucopyranosyl)-D-fructopyranose)-amphotericin B methyl ester (C3)

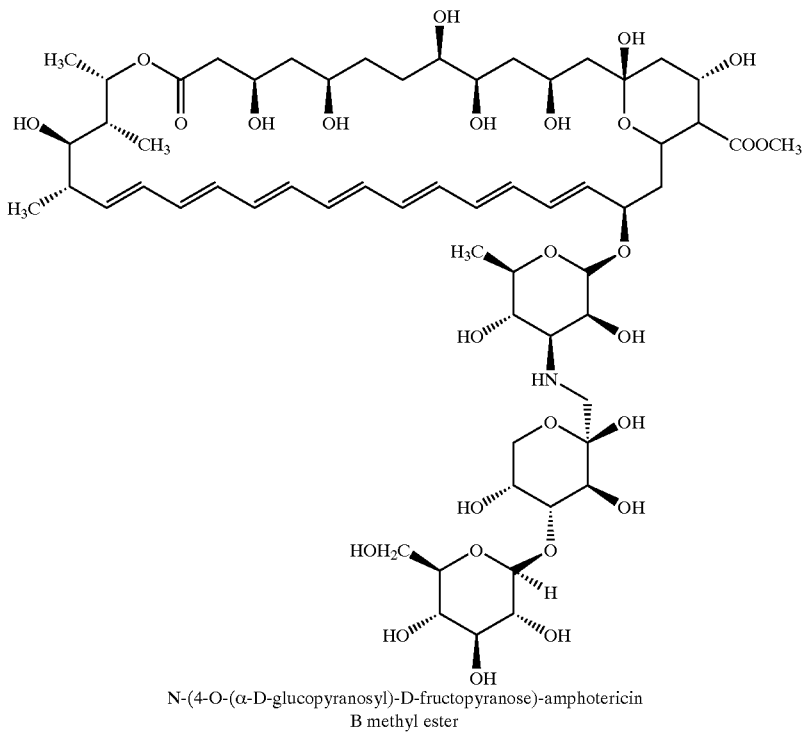

N-(4-O-(α-D-glucopyranosyl)-D-fructopyranose)-amphotericin B methyl ester (C4)

Those of skill in the art will appreciate that many of the compounds encompassed by formula (I), as well as the compound species specifically described herein, may exhibit the phenomena of tautomerism, conformational isomerism, geometric isomerism and/or stereo isomerism. As the formula drawings within this specification and claims can represent only one of the possible tautomeric, conformational isomeric, enantiomeric or geometric isomeric forms, it should be understood that the invention encompasses any tautomeric, conformational isomeric, enantiomeric and/or geometric isomeric forms of the compounds having one or more of the utilities described herein, as well as mixtures of the various different forms.

Moreover, in many of the compounds, the polyene backbone $R^1$ is illustrated with the stereochemistry of many of the chiral centers specified. The specific structures depicted are those that have been reported in the literature for the involved polyene backbones, and are not intended as limiting. Thus, it will be understood that the illustrated structures are intended merely as a short-hand way to represent the actual compound, and to the extent it may be found at a later date these structural representations are incorrect, they are not intending to be limiting in any way.

The polyene macrolide derivatives of the invention may be synthesized according to well-known methods using well-known chemistries. In one embodiment, the polyene macrolide derivatives of formula (I) may be synthesized according to Scheme (I), illustrated below:

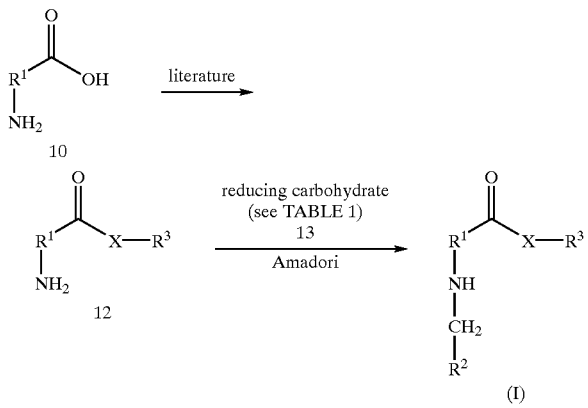

In Scheme (I), $R^1$, $R^2$, $R^3$ and X are as defined for structural formula (I). According to Scheme (I), a core polyene macrolide having a carboxyl and an amino functionality 10 is converted to the corresponding ester, thioester or amide 12 (depending upon the identity of X) using standard methods that are well known in the art. Ester, thioester or amide 12 is reacted with a reducing carbohydrate 13, for example one of the reducing carbohydrates listed in TABLE 1, supra, under Amadori rearrangement conditions to yield polyene macrolide derivatives according to formula (I). The Amadori rearrangement reaction is described in detail in Amadori, 1955, Adv. Carbohydr. Chem. 10:169 and Hodge & Fisher, supra, both of which are incorporated herein by reference.

Core polyene macrolide 10 may be obtained commercially or may be isolated or synthesized according to well-known methods. Methods of synthesizing a variety of core polyene macrolides 10 are described in Beau, "Polyene Macrolides: Stereostructural Elucidation and Synthetic Studies of a Few Members," In: Recent Progress in the Chemical Synthesis of Antibiotics, pp. 135–182, Springer-Verlag, Berlin (1990), as well as the references cited therein. These methods may be routinely adapted to synthesize a wide variety of core polyene macrolides 10. Methods of isolating core polyene macrolides 10 as natural products are well-known in the art.

Ester, thioester or amide 12 may be obtained from core polyene macrolide 10 according to well-known methods. For example, U.S. Pat. No. 4,035,567 describes a process for producing AME. Processes for preparing alkyl esters of core polyene macrolide 10 are described in U.S. Pat. Nos. 3,780,173, 4,035,568, 4,038,382 and 4,365,058. Specific methods for preparing alkyl esters of patricin are described in U.S. Pat. No. 3,961,047. Any of these methods can be routinely modified to produce the corresponding arylalkyl esters, as well as the corresponding alkyl and arylalkyl thioesters.

Methods of synthesizing amides of core polyene macrolide 10 are described in U.S. Pat. No. 4,783,527. Specific methods of synthesizing amides of AmB are described in Czerwinski et al., 1990, J. Antibiot. 43(6):680–683 and Jarzebski et al., 1982, J. Antibiot. 35(2):220–229. Specific methods of synthesizing amides of patricins are described in U.S. Pat. Nos. 5,298,495, 5,296,597 and Bruzzese et al., 1996, J. Med. Chem. 31:965–972. Any of these methods may be routinely adapted to synthesize the full range of amides 13. All of the above-listed patents and references, as well as the various patents and references cited therein, are incorporated herein by reference.

In some instances, ester, thioester or amide 12 may be commercially available. For example, AME is commercially available from Karykion, Princeton, N.J.

In Scheme (I), the formation of polyene macrolide derivatives according to formula (I) by reaction of compound 12 and reducing carbohydrate 13 proceeds in two steps. In the first step, a glycosylamine (not shown) is formed by condensation of the amine group of 12 with the anomeric carbon of reducing carbohydrate 13. In the second step, the glycosylamine is rearranged in an acidic medium to form the polyene macrolide derivatives of structural formula (I).

As previously discussed, the choice of reducing carbohydrate 13 will depend upon the identity of the desired carbohydrate residue $CH_2$—$R^2$. As the reaction proceeds via an Amadori rearrangement, a reducing carbohydrate reactant that will yield the desired carbohydrate residue $CH_2$—$R^2$ should be selected. The principles of the Amadori rearrangement are well-known and briefly illustrated supra. Thus, choosing an appropriate reducing carbohydrate 13 will be apparent to those of skill in the art. Specific exemplary reducing carbohydrates 13 are provided in TABLE 1. Additional guidance can be found in Amadori, 1955, Adv. Carbohydr. Chem. 10:169, Hodge & Fisher, supra, (and the referenced cited therein) and U.S. Pat. No. 5,314,999, all of which are incorporated herein by reference.

Numerous patents and literature references indicate that the Amadori rearrangement may be carried out in an anhydrous solvent system. However, it will be appreciated that since the Amadori rearrangement is acid-catalyzed, and many of the described rearrangement reactions involve polyene macrolides having an acidic carboxyl substituent, these carboxyl-containing polyene macrolides can "self-catalyze" the rearrangement. Anhydrous solvent systems may be used for these "self-catalyzed" Amadori rearrangement reactions.

However, unlike many of the Amadori rearrangements reported in the literature, in the method of Scheme (I), derivatives 12 do not have a free carboxyl group. Rather, this carboxyl has been reacted to form an ester, thioester or amide. Thus, derivatives 12 may not efficiently "self-catalyze" the Amadori rearrangement. As a consequence, it has been discovered that it is preferable to conduct the Amadori rearrangement reaction between derivative 12 and reducing carbohydrate 13 in the presence of water. While the reaction will proceed under anhydrous conditions, significantly better yields are obtained under non-anhydrous conditions. A variety of non-anhydrous solvent systems may be used for Scheme (I). Typically, the solvent system should comprise about 1% (v/v) to 5% (v/v) water. The proton donor may be the solvent system or it may be an added compound, as described in Hodge & Fisher, supra. Any of the solvent systems described in the literature may be adapted for use as described herein. Exemplary solvent systems that may be readily adapted to the principles taught herein are described in Hodge & Fisher, 1963, supra. Specific solvent systems are provided in the Examples section, infra.

Moreover, the literature reports that the Amadori rearrangement may be successfully performed with a 1:1 molar ratio of compounds 12 and 13. However, the Applicants have discovered that using a 1:2 molar ratio of compounds 12 and 13 increases the reaction yield. Thus, while the Amadori rearrangement reaction illustrated in Scheme (I) may be performed with 1–2 equivalents of reducing carbohydrate 13, using 2 equivalents of reducing carbohydrate 13 is preferred.

As a specific example of the Amadori rearrangement reaction, Scheme (II) below illustrates the synthesis of N-tagatopyranose-amphotericin B methyl ester (Compound C1) from AME (12) and α-D glucose (13):

AmB and AME. Generally, active polyene macrolide derivatives of the invention are identified using in vitro screening assays that are well-known in the art. Specific in vitro screening assays that can be used to assess activity are provided in the Examples section.

Alternatively, the polyene macrolide derivatives of the invention may be assessed for antifungal activity using in vivo models. Again, such models are well-known in the art. Other assays as are well known in the art, or that will become apparent to those having skill in the art upon review of this disclosure, may also be used to identify active polyene macrolide derivatives of the invention.

Generally, active polyene macrolide derivatives of the invention will exhibit minimum inhibitory concentrations

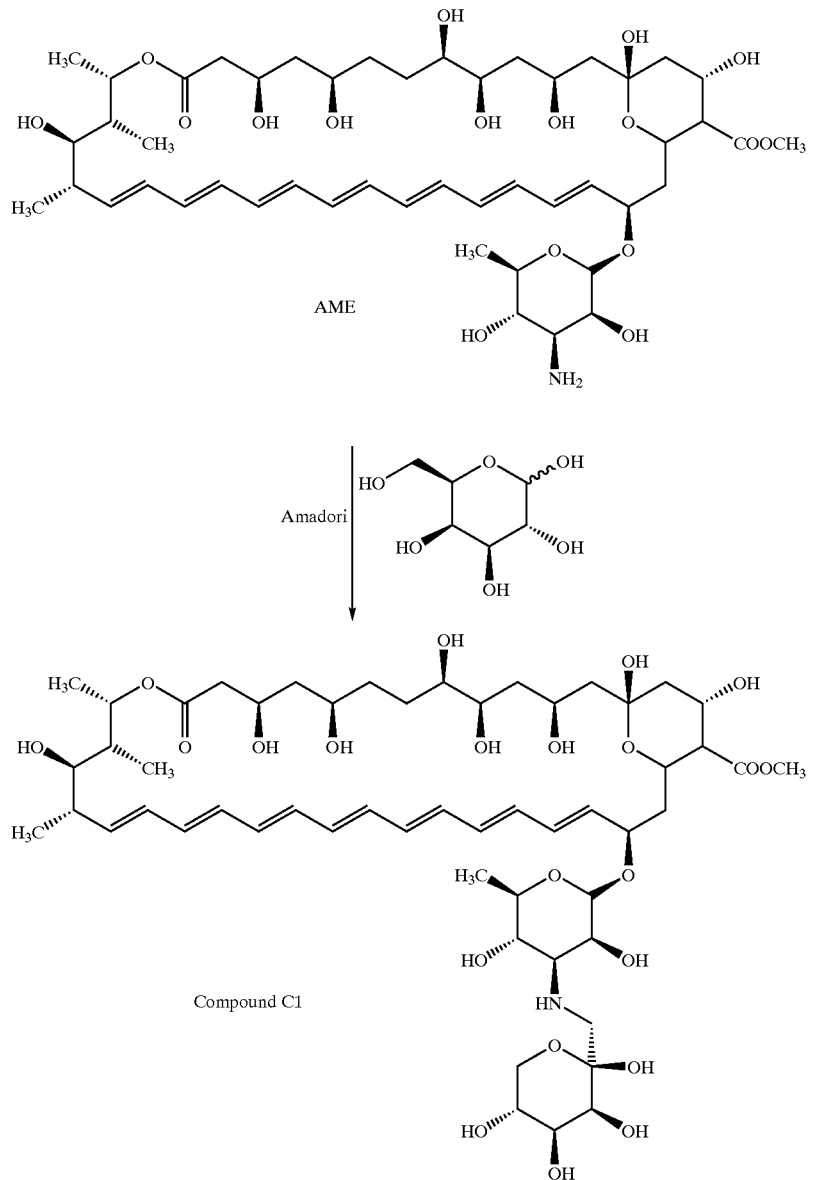

The polyene macrolide derivatives of the invention exhibit significant antifungal activity. Indeed, some of the polyene macrolide derivatives according to formula (I) exhibit significantly higher antifungal activity than both (MICs) of less than about 64 µg/mL, usually less than about 32 µg/mL, preferably less than about 16 µg/mL and most preferably less than about 4 µg/mL against *Candida albicans* using standard methods. Of course, compounds having MICs on the low end of these ranges, or even lower, are preferred. Most preferred for use in treating or preventing systemic infections are polyene macrolide derivatives that exhibit significant antifungal activity, high water-solubility and low toxicity. Toxicity is less of a concern for typical administration, as is water solubility.

The polyene macrolide derivatives of the present invention have significant advantages over currently available polyene macrolide antifungals. Specifically, the polyene macrolide derivatives of the present invention show excellent water solubility, low toxicity, and effective therapeutic potency. Moreover, these glycosyl AME derivatives exhibit antifungal activity comparable to AmB in both in vitro and in vivo assays, and quite unexpectedly have a higher therapeutic index.

The polyene macrolide derivatives according to the invention can be used in a wide variety of applications to inhibit the growth of or kill fungi. For example, the polyene macrolide derivatives can be used as disinfectants or as preservatives for materials such as foodstuffs, cosmetics, medicaments and other nutrient-containing materials.

For use as a disinfectant or preservative the polyene macrolide derivatives can be added to the desired material singly, as mixtures of several polyene macrolide derivatives or in combination with other antifungal and/or antimicrobial agents. The polyene macrolide derivatives may be supplied as the compound per se or may be in admixture with a variety of carriers, diluents or excipients as are well known in the art.

When used to treat or prevent fungal infections the polyene macrolide derivatives of the invention can be administered or applied singly, as mixtures of two or more polyene macrolide derivatives, in combination with other antifungal, antibiotic or antimicrobial agents or in combination with other pharmaceutically active agents. The polyene macrolide derivatives can be administered or applied per se or as pharmaceutical compositions. The specific pharmaceutical formulation will depend upon the desired mode of administration, and will be apparent to those having skill in the art. Numerous compositions for the topical or systemic administration of polyene macrolides are described in the literature. Any of these compositions may be formulation with the polyene macrolide derivatives of the invention.

Pharmaceutical compositions comprising the polyene macrolide derivatives of the invention may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries which facilitate processing of the active polyene macrolide derivatives into preparations which can be used pharmaceutically. Proper formulation is dependent upon the route of administration chosen.

For topical administration the polyene macrolide derivatives of the invention may be formulated as solutions, gels, ointments, creams, suspensions, etc. as are well-known in the art.

Systemic formulations include those designed for administration by injection, e.g. subcutaneous, intravenous, intramuscular, intrathecal or intraperitoneal injection, as well as those designed for transdermal, transmucosal oral or pulmonary administration.

For injection, the polyene macrolide derivatives of the invention may be formulated in aqueous solutions, preferably in physiologically compatible buffers such as Hanks's solution, Ringer's solution, or physiological saline buffer. The solution may contain formulatory agents such as suspending, stabilizing and/or dispersing agents.

Alternatively, the polyene macrolide derivatives may be in powder form for constitution with a suitable vehicle, e.g., sterile pyrogen-free water, before use.

For transmucosal administration, penetrants appropriate to the barrier to be permeated are used in the formulation. Such penetrants are generally known in the art.

For oral administration, the polyene macrolide derivatives can be readily formulated by combining them with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. For oral solid formulations such as, for example, powders, capsules and tablets, suitable excipients include fillers such as sugars, such as lactose, sucrose, mannitol and sorbitol; cellulose preparations such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP); granulating agents; and binding agents. If desired, disintegrating agents may be added, such as the cross-linked polyvinylpyrrolidone, agar, or alginic acid or a salt thereof such as sodium alginate.

If desired, solid dosage forms may be sugar-coated or enteric-coated using standard techniques.

For oral liquid preparations such as, for example, suspensions, elixirs and solutions, suitable carriers, excipients or diluents include water, glycols, oils, alcohols, etc. Additionally, flavoring agents, preservatives, coloring agents and the like may be added.

For buccal administration, the compositions may take the form of tablets, lozenges, etc. formulated in conventional manner.

For administration by inhalation, the compounds for use according to the present invention are conveniently delivered in the form of an aerosol spray from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may also be formulated in rectal or vaginal compositions such as suppositories or retention enemas, e.g, containing conventional suppository bases such as cocoa butter or other glycerides.

In addition to the formulations described previously, the polyene macrolide derivatives may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

Alternatively, other pharmaceutical delivery systems may be employed. Liposomes and emulsions are well known examples of delivery vehicles that may be used to deliver the polyene macrolide derivatives of the invention. Certain organic solvents such as dimethylsulfoxide also may be employed, although usually at the cost of greater toxicity. Additionally, the polyene macrolide derivatives may be delivered using a sustained-release system, such as semi-permeable matrices of solid polymers containing the therapeutic agent. Various of sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

As certain of the hydroxyls on the polyene macrolide derivatives of the invention may be acidic, or the carbohydrate residue may include acidic or basic substituents, the polyene macrolide derivatives may be included in any of the above-described formulations as the free acids, the free bases or as pharmaceutically acceptable salts. Pharmaceutically acceptable salts are those salts which retain substantially the antifungal activity of the free acids or bases and which are prepared by reaction with bases or acids, respectively. Pharmaceutical salts tend to be more soluble in aqueous and other protic solvents than are the corresponding free base or acid forms.

The polyene macrolide derivatives of the invention, or compositions thereof, will generally be used in an amount effective to achieve the intended purpose. Of course, it is to be understood that the amount used will depend on the particular application.

For example, for use as a disinfectant or preservative, an antifungally effective amount of a polyene macrolide derivative, or composition thereof, is applied or added to the material to be disinfected or preserved. By antifungally effective amount is meant an amount of polyene macrolide derivative or composition that inhibits the growth of, or is lethal to, a target fungi. While the actual amount will depend on a particular target fungi and application, for use as a disinfectant or preservative the polyene macrolide derivatives, or compositions thereof, are usually added or applied to the material to be disinfected or preserved in relatively low amounts. Typically, the polyene macrolide derivative comprises less than about 5% by weight of the disinfectant solution or material to be preserved, preferably less than about 1% by weight and more preferably less than about 0.1% by weight. An ordinarily skilled artisan will be able to determine antifungally effective amounts of particular polyene macrolide derivatives for particular applications without undue experimentation using, for example, the in vitro assays provided in the examples.

For use to treat or prevent fungal infections, the polyene macrolide derivatives of the invention, or compositions thereof, are administered or applied in a therapeutically effective amount. By therapeutically effective amount is meant an amount effective ameliorate the symptoms of, or ameliorate, treat or prevent fungal infections. Determination of a therapeutically effective amount is well within the capabilities of those skilled in the art, especially in light of the detailed disclosure provided herein.

As in the case of disinfectants and preservatives, for topical administration to treat or prevent fungal infections, a therapeutically effective dose can be determined using, for example, the in vitro assays provided in the examples. The treatment may be applied while the infection is visible, or even when it is not visible. An ordinarily skilled artisan will be able to determine therapeutically effective amounts to treat topical infections without undue experimentation.

For systemic administration, a therapeutically effective dose can be estimated initially from in vitro assays. For example, a dose can be formulated in animal models to achieve a circulating polyene macrolide derivative concentration range that includes the $I_{50}$ as determined in cell culture (i.e., the concentration of test compound that is lethal to 50% of a cell culture), the MIC, as determined in cell culture (i.e., the minimal inhibitory concentration for growth) or the $I_{100}$ as determined in cell culture (i.e., the concentration of polyene macrolide derivative that is lethal to 100% of a cell culture). Such information can be used to more accurately determine useful doses in humans.

Initial dosages can also be estimated from in vivo data, e.g., animal models, using techniques that are well known in the art. One having ordinary skill in the art can readily optimize administration to humans based on animal data.

Alternatively, initial dosages can be determined from the dosages administered of known polyene macrolides by comparing the $IC_{50}$, MIC and/or $I_{100}$ of the specific polyene macrolide derivative with that of a known polyene macrolide, and adjusting the initial dosages accordingly. The optimal dosage may be obtained from these initial values by routine optimization.

Dosage amount and interval may be adjusted individually to provide plasma levels of the active polyene macrolide derivative which are sufficient to maintain therapeutic effect. Usual patient dosages for administration by injection range from about 0.1 to 5 mg/kg/day, preferably from about 0.5 to 1 mg/kg/day. Therapeutically effective serum levels may be achieved by administering multiple doses each day.

In cases of local administration or selective uptake, the effective local concentration of polyene macrolide derivative may not be related to plasma concentration. One having skill in the art will be able to optimize therapeutically effective local dosages without undue experimentation.

The amount of polyene macrolide derivative administered will, of course, be dependent on the subject being treated, on the subject's weight, the severity of the affliction, the manner of administration and the judgment of the prescribing physician.

The antifungal therapy may be repeated intermittently while infections are detectable or even when they are not detectable. The therapy may be provided alone or in combination with other drugs, such as for example other antifungals, antibiotics or antimicrobials, or other polyene macrolide derivatives of the invention.

Preferably, a therapeutically effective dose of the polyene macrolide derivatives described herein will provide therapeutic benefit without causing substantial toxicity. Toxicity of the polyene macrolide derivatives can be determined using standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. Polyene macrolide derivatives which exhibit high therapeutic indices are preferred. The data obtained from these cell culture assays and animal studies can be used in formulating a dosage range that is not toxic for use in human. The dosage of the polyene macrolide derivatives described herein lies preferably within a range of circulating concentrations that include the effective dose with little or no toxicity. The dosage may vary within this range depending upon the dosage form employed and the route of administration utilized. The exact formulation, route of administration and dosage can be chosen by the individual physician in view of the patient's condition. See, e.g., Fingl et al., 1975, In: *The Pharmacological Basis of Therapeutics,* Ch. 1, p. 1.

The invention having been described, the following examples are presented to illustrate, rather than to limit, the scope of the invention. The examples illustrate various embodiments and features of the present invention.

EXAMPLE 1

Preparation at Glycosyl Derivates of AME/AmB

This example demonstrates the preparation of various glycosyl derivatives of AME according to the present invention and, for comparison, corresponding glycosyl derivatives of AmB. AmB was purchased from Biosource Pharm, Spring Valley, N.Y. AME was purchased from Karykion, Princeton, N.J. Using the procedure described in Falkowski et al., J. Antibiot. 28:244, approximately 100 mg of AME or AmB was added to each of the reducing sugars given in TABLE 2 below in approximately 1.5 ml of DMF.

TABLE 2

Preparation of Glycosyl Derivatives of AME/AmB

| Cmpd Number | Reducing Sugar | C AME | B AmB #1 | A AmB #2 |
|---|---|---|---|---|
| (1) | D-Galactose | 20.0 mg | 20.0 mg | 20.1 mg |
| (2) | α-D-lactose monohydrate | 39.0 mg | 39.0 mg | 38.7 mg |
| (3) | D-cellobiose | 38.5 mg | 36.7 mg | 37.6 mg |
| (4) | D-maltosemonohydrate | 40.0 mg | 39.5 mg | 40.0 mg |

Referring to Scheme (I), 1–2 equivalents of the reducing sugar (13) may be used per equivalent of polyene macrolide derivative (12). However, it has been found that using 2 equivalents provides better yields. After approximately 23 hours, the solutions were precipitated with ether and washed with ether 3 times. The product was refrigerated for approximately 60 hours to allow the product to dry. The product was then lyophilized, and HPLC analysis was conducted for each product. The compounds produced in group C are identified as C1–C4 and correspond to compounds C1–C4 given in the text above as preferred compounds of the present invention. Compounds in group B are identified as B1–B4, and compounds from group A are identified as A1–A4.

As shown in TABLE 2, two sets of samples were prepared using AmB (sets B and A). In contrast to set A, set B was further methylated to produce the corresponding methyl ester and to add a methyl group at the N position using the following procedure. Approximately 7.2 g of diazald was dissolved in 0.5 ml of water in a flask, which produced a slush-type mixture. A syringe was used to add 6M NaOH dropwise until the total volume of the mixture was approximately 30 ml. The mixture was allowed to react until the ether, contained in a test tube and connected to the flask to allow the gas produced from the reaction to pass to the test tube, turned a deep yellow color. Approximately 2 ml of the ether/$CH_2N_2$ solution was then added to each sugar derivative, followed by approximately 3 ml of DMF, and then another 3 ml of the ether/$CH_2N_2$ solution. These mixtures were allowed to react for approximately 3 hours. Each product was precipitated with a ether solution made from the ether/$CH_2N_2$ solution and supernatant. The products were precipitated and then placed on the lyophilizer for approximately 12 hours.

Mass spectrometry and HPLC analyses were conducted to verify the composition of each compound produced. HPLC analyses were conducted using an HP 1090 analytical HPLC (Waters Symmetry C-18, particle size 3.5 μm, 4.6×50 mm, Cat. No. WAT200625) using a linear gradient of 35% to 55% Solvent B (100 mM Triethylammonium acetate in 90% acetonitrile pH 7) in Solvent A (100 mM Triethylammonium acetate pH 7) over 10 minutes at a flow rate of 1.1 mL/min. HPLC peaks were observed by UV. The retention times of the peaks are provided in TABLE 3.

For each compound Minimum Inhibitory Concentrations (MIC) were determined as described in Reference Method for Broth Dilution Antifungal Susceptibility Testing of Yeasts; Approved Standard; NCCLS document M27-A (ISBN 1-56238-328-0); NCCLS, 940 West Valley Road, Suite 1400, Wayne, Pa. 19087, 1997. Also, Minimum Fungicidal Concentrations (MFC) were made using material obtained from the well defining the MIC and at least 3 compound dilutions lower than the MIC. Ten microliter samples were removed from the corresponding wells and deposited onto blood agar plates. Plates were incubated at 35° C. for 48 hours. The highest compound dilution at which no colonies are apparent on the plate was considered the MFC. Maximum non-lethal dose (NLD) data were also obtained for each product by initially intravenously administering a single 16 mg/kg dose to each of 4 mice in several groups. After review of findings, higher or lower doses were administered and a maximum non-lethal dose was determined. $Ed_{50}$ data were also obtained for each compound. Efficacy was evaluated in mice injected with C. albicans. Therapeutic efficacy was defined as a 2 log reduction in kidney cfu relative to mean vehicle control. The proportion of animals exhibiting the therapeutic effect was determined using Graph Pad Prism software.

TABLE 3 shows the results from these tests, where compounds from group C in TABLE 2 are listed as C1–C4, compounds from group B are listed as B1–B4, and compounds from group A are listed as A1–A4. Data are also shown for AmB and AME for comparison. As noted previously, compounds C1–C4 are compounds of the present invention and as shown in TABLE 3, these compounds exhibit surprisingly superior results than AmB and AME. Compounds C1–C4 exhibit higher MICs and NLDs than AME and extremely higher MICs and NLDs than AmB. Compounds C1–C4 also exhibit higher water solubility than AME and extremely higher water solubility than AmB. Moreover, while the compounds have comparable antifungal activity to AmB, they exhibit better therapeutic indices.

TABLE 3

HPLC, Water Solubility, Potency, and NLD Results
for Various Glycosyl Derivatives of AME Compared to Glycosyl Derivatives of AmB

| Cmpd Name | Cmpd MW | HPLC Retention Time AMP3555A | HPLC Crude Prod. Purity AMP355A 400 nm | Micro. Data (DLM/CJ) MIC | Micro. Data (DLM/CJ) MFC | NLD (mg/kg) | ED$_{50}$ Kidney CFU Red. (mg/kg) | Water Sol. (mg/mL) |
|---|---|---|---|---|---|---|---|---|
| AmB | 924 | 3.216 | 93.4 | 0.5 | 2 | 2–4* | 3.582 | negligible |
| AME | 938 | 7.423 | 77.0 | 1 | 2 | | 9685 | 10 |
| C1 | 1100 | 7.293 | 45.0 | 2 | 2 | >64 | <3 | >16 |
| C2 | 1262 | 7.279 | 52.7 | 2 | 2 | >64 | <3 | >16 |
| C3 | 1262 | 7.262 | 48.8 | 2 | 2 | >64 | 13.63 | >16 |
| C4 | 1262 | 7.328 | 47.8 | 2 | 2 | >64 | 10.13 | >16 |
| B1 | 1114 | 7.558 | 37.7 | 2 | 4 | >64 | | <2.8 |
| B2 | 1276 | 6.755 | 36.3 | 4 | 4 | 32 | | <2.8 |
| B3 | 1276 | 6.860 | 42.6 | 4 | 4 | >64 | | <2.8 |
| B4 | 1276 | 6.710 | 39.1 | 4 | 4 | >64 | | <2.8 |
| A1 | 1086 | 2.314 | 66.9 | 4 | 4 | 8 | | <1.4 |
| A2 | 1248 | 1.801 | 69.4 | 4 | 4 | 8 | | <1.4 |
| A3 | 1248 | 1.753 | 58.5 | 4 | 4 | 8 | | <1.4 |
| A4 | 1248 | 1.721 | 69.3 | 4 | 4 | 8 | | <1.4 |

*literature value

EXAMPLE 2

Therapeutic Effect of Various Glycosyl Derivatives of AME

FIG. 1 shows the level of *Candida albicans* in the kidneys of mice treated with various compounds of the present invention. As shown the concentration of *Candida albicans* is significantly lower in those mice treated compounds C1 and C2 than for AME.

The invention now having been fully described, it will be apparent to one of ordinary skill in the art that many changes and modifications can be made thereto without departing from the spirit or scope of the appended claims.

We claim:

1. A polyene macrolide of formula I:

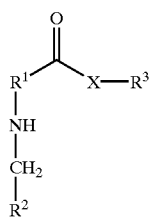

(I)

or a pharmaceutically acceptable salt thereof, wherein
$R^1$ is a polyene backbone;
$CH_2$—$R^2$ is a carbohydrate residue, wherein the $CH_2$ is the anomeric carbon of a terminal carbohydrate saccharide;
$R^3$ is alkyl or arylalkyl; and
X is O or S,
with the proviso that when $R^1$ is a polyene backbone derived from amphotericin B, X is O, and $R^3$ is methyl, then $R^2$ is other than fructosyl.

2. The polyene macrolide of claim 1, wherein $R^1$ is a polyene backbone derived from amphotericin B, aureofacin, candicidin, candidin, levorin, mycoheptin, nystatin, partricin, perimycin, pimaricin, polyfungin, rimocidin or trichomycin.

3. The polyene macrolide of claim 2, wherein $R^1$ is a polyene backbone derived from amphotericin B or nystatin.

4. The polyene macrolide of claim 1, wherein X is O.

5. The polyene macrolide of claim 1, wherein $CH_2$—$R^2$ is an Amadori rearrangement product of a reducing carbohydrate selected from the group consisting of 3-O-methyl-glucose, 4,6-di-O-methyl-D(L)-mannose, 4,6-O-benzylidene-D(L)-galactose, 4,6-O-benzylidene-D(L)-glucopyranoside, 4,6-O-ethylidene-α-D(L)-glucose, 4-azidomethyl-tetrahydro-pyran-2,3,5-triol, 4-benzyloxy-6-benzyloxymethyl-tetrahydro-pyran-2,3,5-triol, 4-fluoro-4deoxy-D(L)-glucose, 6-acetamido-6-deoxy-α-D(L)-glucopyranose, 6-aminomethyl-4H-pyran-2,3,4,5-tetraol, 6-chloro-6-deoxy-alpha-D(L) glucopyranose, alginic acid, allose, α-L(D) rhamnose, altrose, arabinose, D(L)-arabinose, D(L)-fucose, D(L)-glucuronic acid, D(L)-leucrose, D(L)-mannose-6-phosphate, D(L)-xylose, D-thevetose, fucose, gentiobiose, glucose, gulose, idose, lyxose, maltopentose, mannose, mannose-6-phosphate, melibiose, N-2,3,5-trihydroxy-6-hydroxymethyl-tetrahydropyran-4-yl)-acetamide panose, pectic acid, rhamnose, ribose, salicin, sorbose, sulfanilamide-N4-D(L)-glucoside talose, and xylose.

6. The polyene macrolide of claim 1, wherein $CH_2$—$R^2$ is a monosaccharide.

7. The polyene macrolide of claim 6, wherein $CH_2$—$R^2$ is selected from the group consisting of glucopyranose, mannopyranose, galactopyranose, fructopyranose and tagatopyranose.

8. The polyene macrolide of claim 1, wherein $CH_2$—$R^2$ is an oligosaccharide or a polysaccharide.

9. The polyene macrolide of claim 8, wherein $CH_2$—$R^2$ is selected from the group consisting of 4-O-(β-D-galactopyranosyl)-D-fructopyranose 4-O-(β-D-glucopyranosyl)-D-fructopyranose 4-O-(α-D-glucopyranosyl)-D-fructopyranose sucrose, maltose, lactose, cellobiose, L-rhinnose and D-ribose.

10. The polyene macrolide of claim 1, wherein $R^3$ is a lower alkyl, a methyl, an allyl, or a benzyl.

11. The polyene macrolide of claim 10, wherein $R^1$ is a polyene backbone derived from amphotericin B.

12. The polyene macrolide of claim 10, wherein $CH_2$—$R^2$ is selected from the group consisting of 4-O-(β-D- galactopyranosyl)-D-fructopyranose 4-O-(β-D-glucopyranosyl)-D-fructopyranose and 4-O-(α-D-glucopyranosyl)-D-fructopyranose.
13. The polyene macrolide of claim 1, which has the formula:
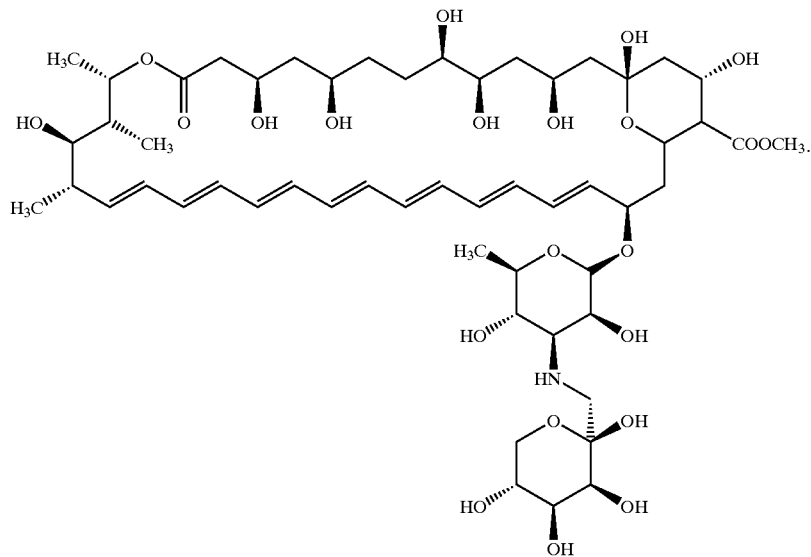
14. The polyene macrolide of claim 1, which has the formula:
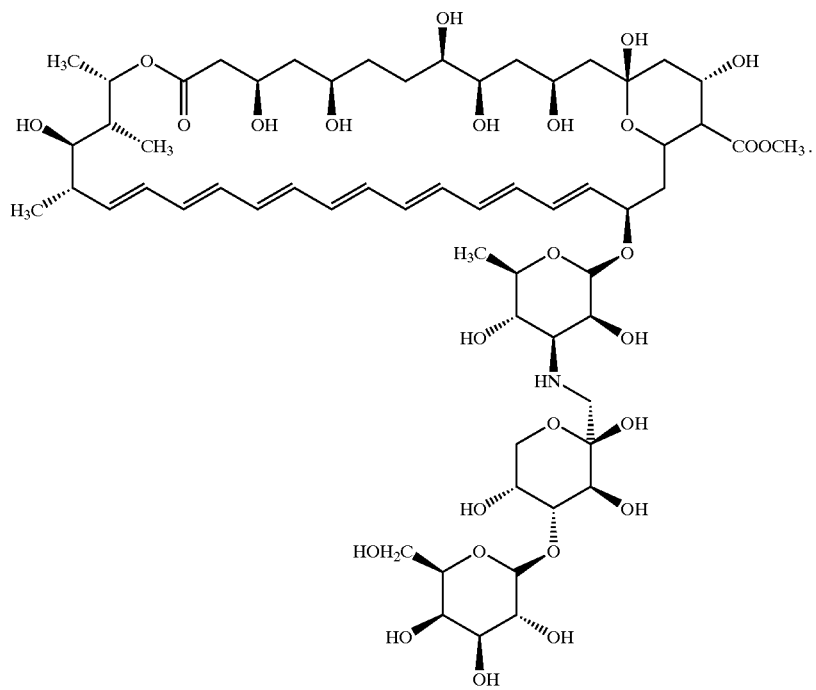

15. The polyene macrolide of claim 1, which has the formula:
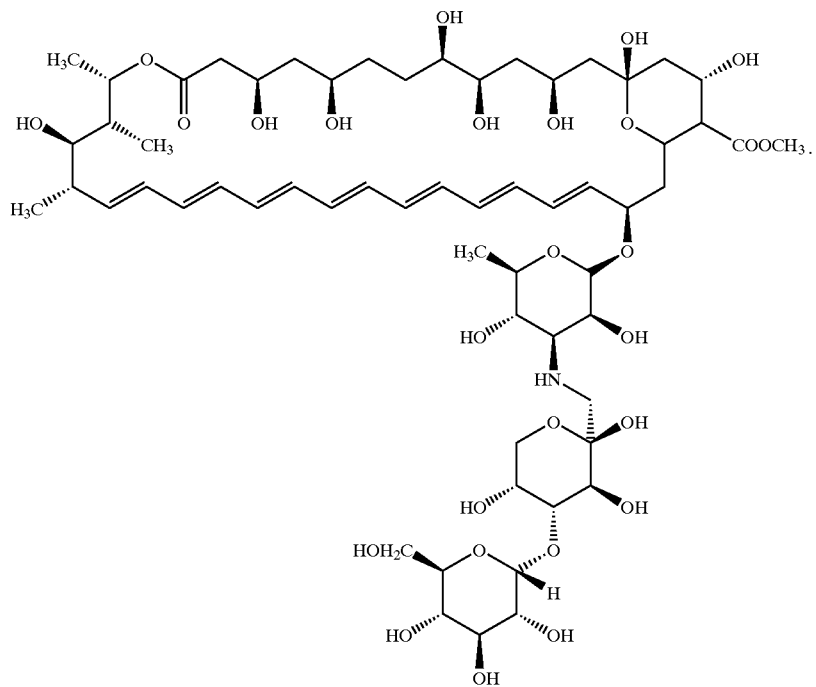
16. The polyene macrolide of claim 1, which has the formula:
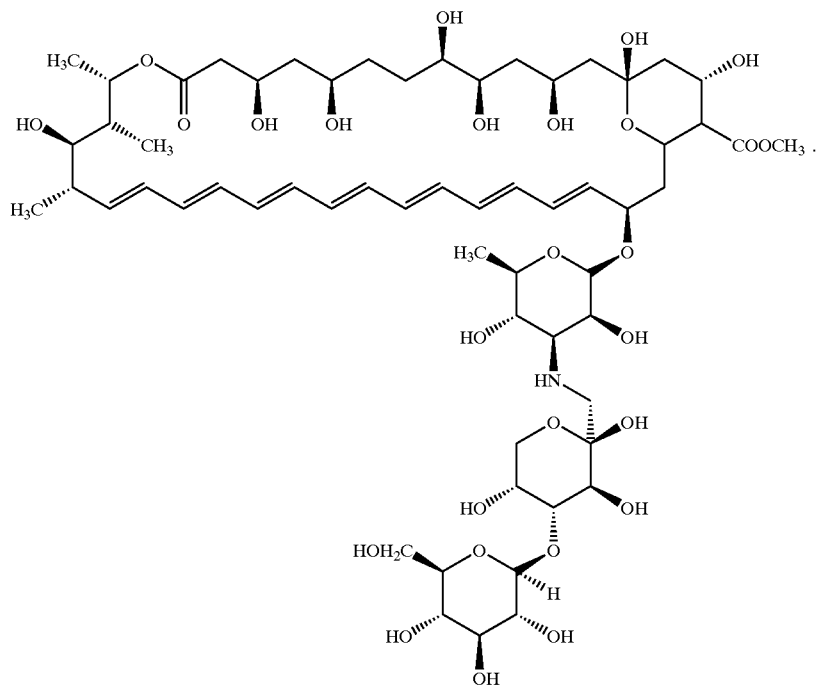

17. A method of making a polyene macrolide derivative according to claim 1, comprising reacting an ester or thioester polyene macrolide derivative according to structural formula (II):

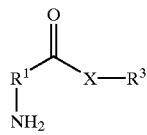
(II)

wherein $R^1$, X and $R^3$ are as previously defined in claim 1, with a reducing carbohydrate under Amadori rearrangement conditions.

18. The method of claim 17, in which the molar ratio of reducing carbohydrate to ester or thioester polyene macrolide derivative is about 2:1.

19. The method of claim 17 in which the reaction is carried out under non-anhydrous conditions.

20. The compound produced by the method of claim 17, wherein when $R^1$ is derived from amphotericin B, X is O and $R^3$ is methyl, lower alkanyl or lower alkyl, then the reducing carbohydrate is not D-mannose or α-D-glucose.

21. A pharmaceutical composition comprising a polyene macrolide derivative according to claim 1 and a pharmaceutically acceptable carrier, diluent, or excipient.

22. A method for treating a fungal infection, comprising the step of administering to a host in need thereof a therapeutically effective amount of a polyene macrolide of formula (III):

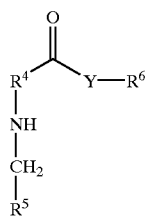
(III)

or a pharmaceutically acceptable salt thereof, wherein:
  Y is O or S;
  $R^4$ is a polyene backbone;
  $CH_2$—$R^5$ is a carbohydrate residue, wherein the $CH_2$ is the anomeric carbon of a terminal carbohydrate saccharide; and
  $R^6$ is alkyl or arylalkyl.

23. The method of claim 22 wherein said polyene macrolide is administered by topical application.

24. The method of claim 22 with the proviso that when R is a polyene backbone derived from amphotericin B, Y is O and $R^6$ is methyl, then $R^5$ is other than fructosyl.

25. The method of claim 24 wherein in said polyene macrolide $R^6$ is lower alkyl, methyl, allyl or benzyl and $CH_2$—$R^5$ is selected from the group consisting of 4-O-(β-D-galactopyranosyl)-D-fructopyranose, 4-O-(β-D-glucopyranosyl)-D-fructopyranose, and 4-O-(α-D-glucopyranosyl)-D-fructopyranose.

26. The method of claim 22 wherein said polyene macrolide has the formula:

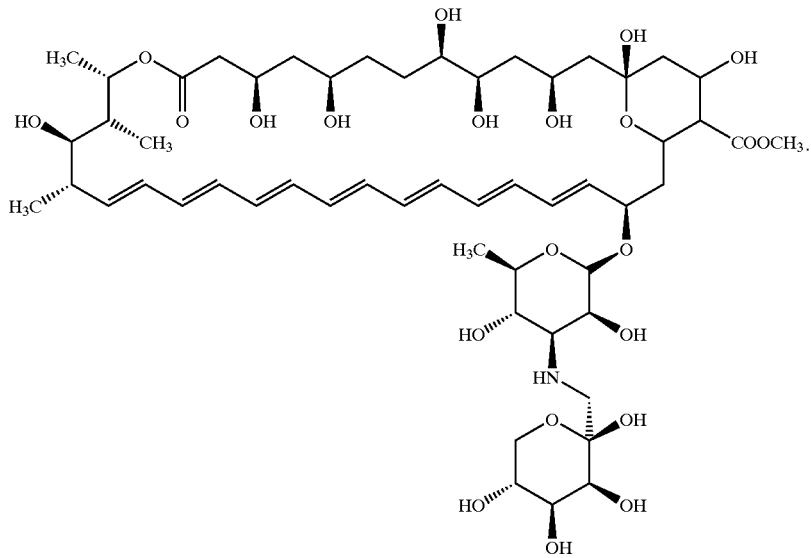

27. The method of claim 22 wherein said polyene macrolide has the formula:
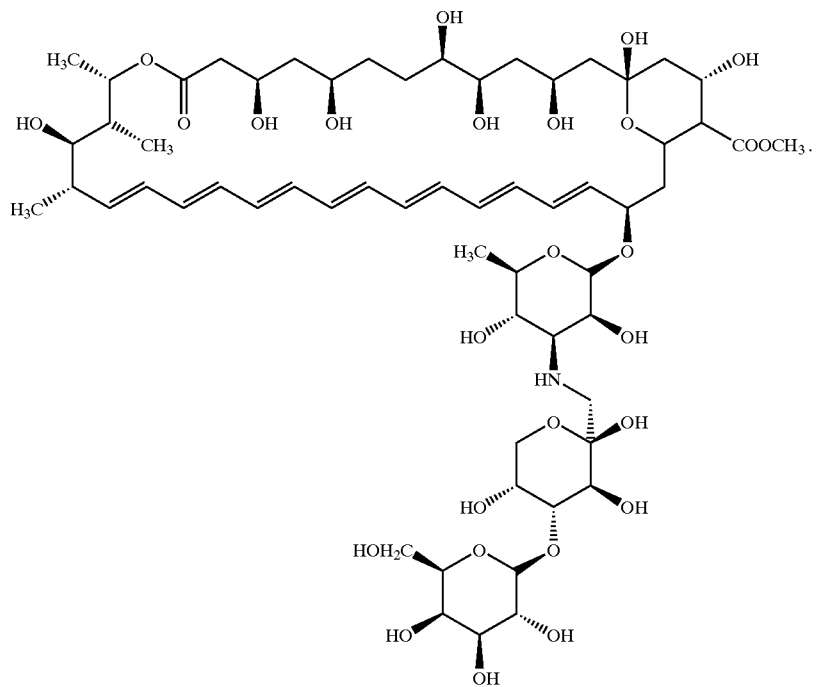
28. The method of claim 22 wherein said polyene macrolide has the formula:
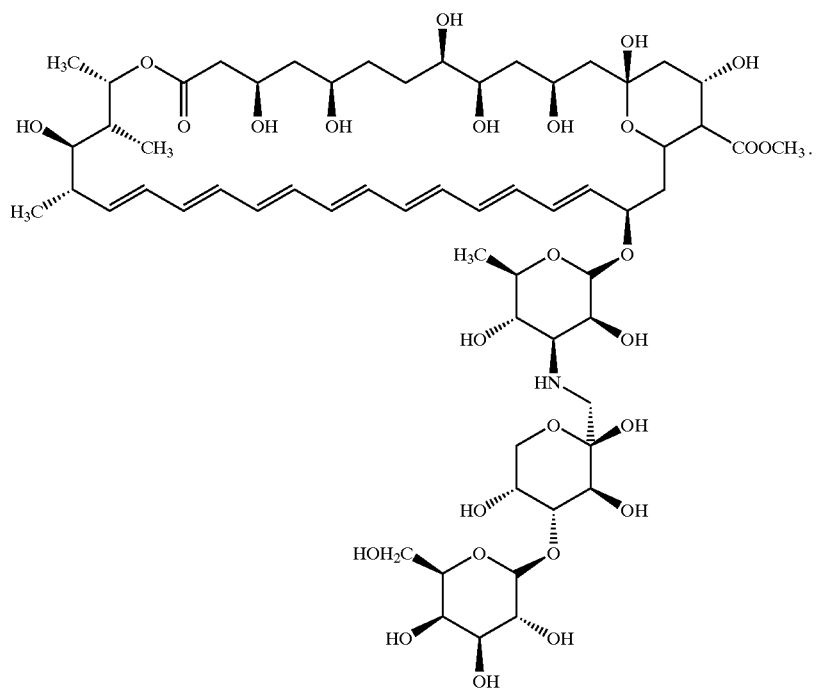

29. The method of claim 22 wherein said polyene macrolide has the formula:

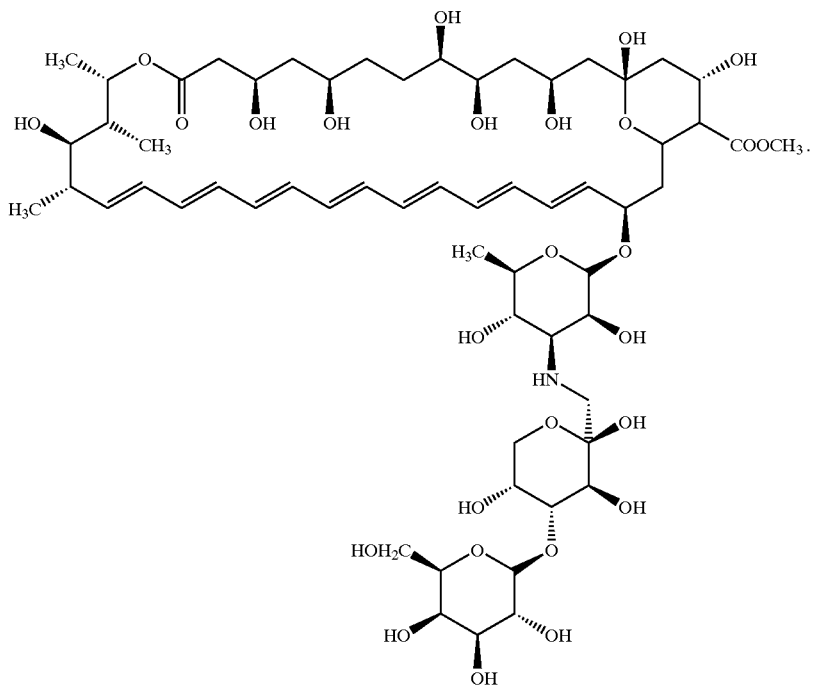

30. A method of preventing a fungal infection, comprising the step of administrating to a subject an effective amount of a polyene macrolide of structure (III):

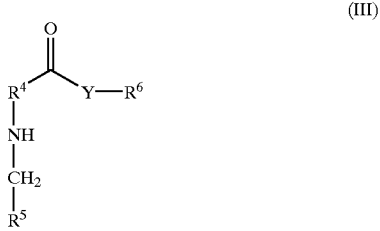

(III)

or a pharmaceutically acceptable salt thereof, wherein
Y is O or S;
$R^4$ is a polyene backbone;
$CH_2$—$R^5$ is a carbohydrate residue, wherein the $CH_2$ is the anomeric carbon of a terminal carbohydrate saccharide; and
$R^6$ is alkyl or arylalkyl.

* * * * *